July 22, 1947. P. R. HAGUE Plant Pat. 747
DIANTHUS CARYOPHYLLUS PLANT
Filed March 18, 1946
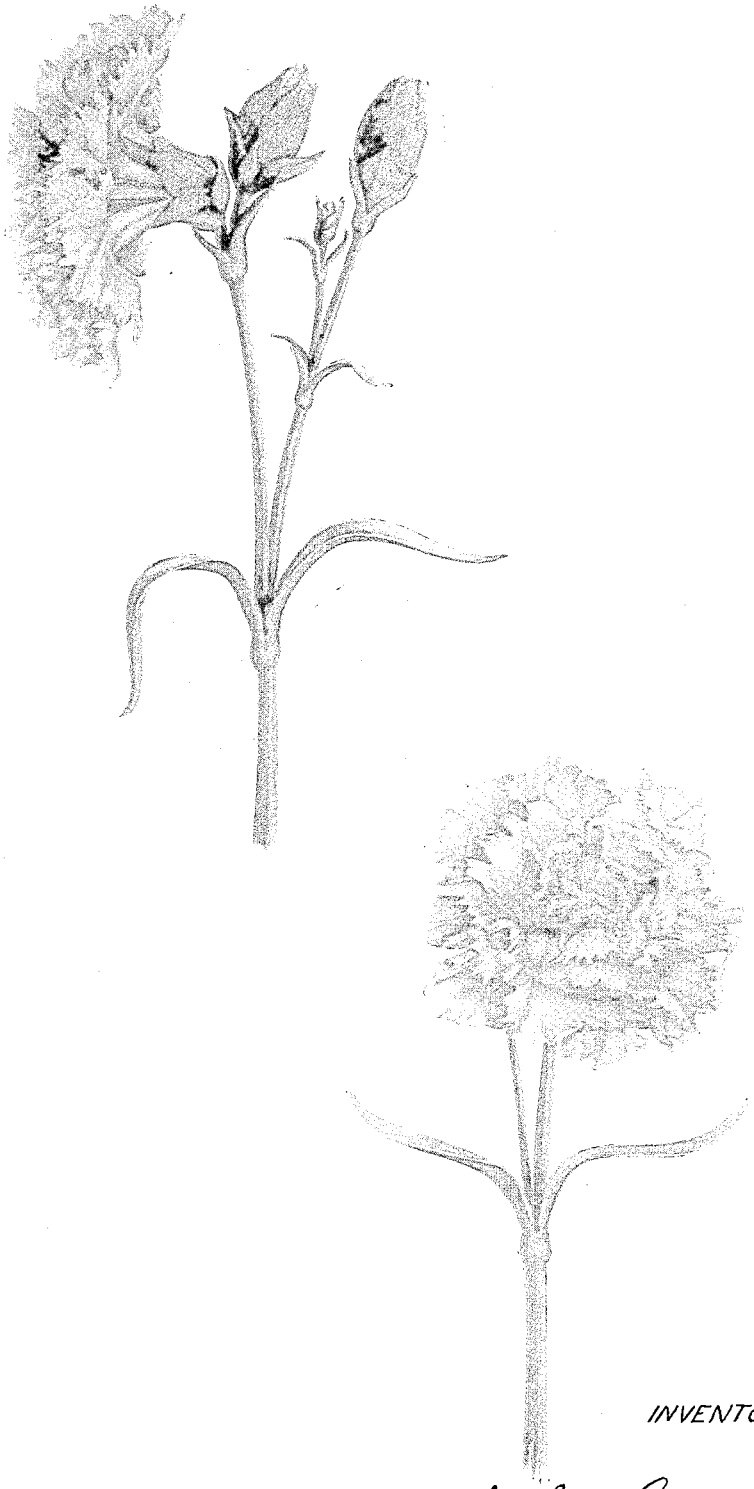
INVENTOR
Phyllis Rene Hague Patented July 22, 1947

UNITED STATES PATENT OFFICE

747

DIANTHUS CARYOPHYLLUS PLANT

Phyllis René Hague, West Hill, East York Township, Ontario, Canada, assignor to Jackson and Perkins Co., Newark, N. Y.

Application March 18, 1946, Serial No. 655,033

1 Claim. (Cl. 47—60)

The present discovery relates to a new variety of *Dianthus caryophyllus* plant which has the general characteristics of *Dianthus caryophyllus* "Mrs. Sinkins," a dianthus well-known in England for at least half a century, which bears pure white flowers but is distinguished by having a pink flower. This variety first appeared among other dianthus seedlings in the discoverer's garden in 1937. It has been asexually reproduced and in each instance came true to form.

The original drawing shows in actual size the new variety in side view and front view.

The following is a detailed description of the new variety:

*Plant*

Stout erect stiffish smooth cespitose perennial.

Leaves: Bottom leaves in the plant many in a tuft, three to six inches long, thickish and broad (by comparison with other varieties of dianthus), more or less canaliculate, midrib strong and one weaker nerve on either side, apex long-pointed.

Flower stems: Ten to seventeen inches long, obscurely angled, nodes prominently swollen and covered in the leaf sheath, forked towards the top so that it is usually three to five flowered, most commonly having four.

Colour: Glaucous-blue, but very slightly less blue than other varieties of dianthus.

*Flower*

Flowers mostly on own branched stalks but some of the laterals nearly sessile. Solitary on the branch. In good average soil the first flowers are 2" to 2½" across; later flowers on laterals from 1" to 1¾".

Petals: Average sixty-five in fully grown flowers, ¾" at the widest point, up to 1½" long, contiguous and prominently toothed, slightly more indented than "Mrs. Sinkins." Petals are not bearded in throat but nearly always have a small dark crimson blotch at beginning of throat.

Colour: Bright rose pink, rose-madder with a very faintly mauve tinge, early flowers slightly deeper and brighter than laterals. Individual petals are darkest at tip, merging into paler pink (with crimson blotch) at throat, and then into pale greenish white at claw.

Calyx: Cylindrical, somewhat narrowing towards apex, about one inch long and many-nerved. Teeth erect and blunt-pointed. (Note: A predominant and unvarying characteristic of the new variety in which it resembles "Mrs. Sinkins," is that when the flower is fully opened the calyx splits down one section, usually underneath the flower, exposing the bases of some of the petals.)

Colour of calyx: Yellow-green, teeth usually edged narrowly with brownish-red.

Bracts: Four in number, very broad and scale-like, about one-third the length of the calyx.

Colour of bracts: Similar yellow-green to calyx, but shading to deeper blue-green at tips.

Stamens: Eighteen to twenty, about one inch long.

Colour of stamens: Filaments white, anthers pale greyish-pink.

Ovary: Small, four-sided, pale green. When ripe the seed pod opens at the tip into four sections. It frequently does not seed; when present seeds are seldom more than six in number, black when fully ripe.

Fragrance: Outstandingly sweet and strong, a rich clove perfume which remains when the flower is picked and kept in water and continues until it actually dies. (Perfume exactly resembles that of "Mrs. Sinkins.")

*Season*

Commences to flower about the first week of June and continues from four to five weeks.

*Improvements upon original*

The new variety, although closely resembling Dianthus "Mrs. Sinkins," has several differences from, and improvements upon, the original, in addition to the difference in colour of the flower. The flower stems are slightly thicker and stronger, holding the flowers more erect and making the plant less inclined to straggle. It is very free-flowering, averaging four buds to a flower spike and sixty flower spikes to a clump seven inches across the base. The new variety is somewhat hardier than Dianthus "Mrs. Sinkins," several times having withstood temperatures of thirty degrees below zero, with no covering other than a light snowfall. The discoverer believes that it would stand considerably lower temperatures, as this dianthus has been grown by her for eight years in an exposed, hilltop garden in the open country near Toronto, Canada, where with no winter protection whatever none of these plants has ever winter-killed.

The original plant, from which this variety started, is still in its original place in the garden, having received no special care at all, no winter covering or extra feeding, and in these circumstances has continued to flower freely each season for the past eight years, with no deterioration in the quality of the flowers. The plant is still strong and healthy.

In general appearance, in addition to the brilliance of its colouring, the new variety is altogether more robust, stronger-growing, more compact and floriferous than the variety from which it undoubtedly originated, "Mrs. Sinkins," with slightly larger and more double flowers.

I claim:

The variety of *Dianthus caryophyllus* plant substantially as herein disclosed, having the general characteristics of the variety "Mrs. Sinkins," but distinguished by having a pink flower.

PHYLLIS RENÉ HAGUE.